(12) United States Patent
Yagi et al.

(10) Patent No.: US 7,847,263 B2
(45) Date of Patent: Dec. 7, 2010

(54) RADIATION IMAGING APPARATUS

(75) Inventors: Tomoyuki Yagi, Honjo (JP); Tadao Endo, Honjo (JP); Toshio Kameshima, Kumagaya (JP); Katsuro Takenaka, Honjo (JP); Keigo Yokoyama, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/607,464

(22) Filed: Oct. 28, 2009

(65) Prior Publication Data

US 2010/0044573 A1    Feb. 25, 2010

Related U.S. Application Data

(62) Division of application No. 11/814,749, filed as application No. PCT/JP2007/051535 on Jan. 24, 2007, now Pat. No. 7,629,587.

(30) Foreign Application Priority Data

Jan. 30, 2006  (JP) .............................. 2006-020975
Jan. 12, 2007  (JP) .............................. 2007-004676

(51) Int. Cl.
*G01T 1/20*  (2006.01)
(52) U.S. Cl. ................................ 250/370.15
(58) Field of Classification Search ............ 250/370.15; 378/98.8
See application file for complete search history.

(56) References Cited

U.S. PATENT DOCUMENTS

| | | | |
|---|---|---|---|
| 5,912,943 A | 6/1999 | Deucher et al. | 378/98.8 |
| 5,940,470 A | 8/1999 | Palm-Plessman et al. | 378/197 |
| 6,952,015 B2 | 10/2005 | Kameshima | 250/370.11 |
| 6,952,464 B2 | 10/2005 | Endo | 378/98.11 |
| 6,985,555 B2 | 1/2006 | Endo | 378/98.11 |
| 7,002,157 B2 | 2/2006 | Kameshima | 250/370.11 |
| 7,012,260 B2 | 3/2006 | Endo | 250/370.11 |
| 7,138,639 B2 | 11/2006 | Kameshima | 250/370.11 |
| 7,154,099 B2 | 12/2006 | Endo | 250/370.11 |
| 7,227,926 B2 | 6/2007 | Kameshima et al. | 378/98.9 |

(Continued)

FOREIGN PATENT DOCUMENTS

DE    102004022804 B3    9/2005

(Continued)

OTHER PUBLICATIONS

Extended European Search Report for counterpart EPA 07707753.5.

*Primary Examiner*—Constantine Hannaher
(74) *Attorney, Agent, or Firm*—Fitzpatrick, Cella, Harper & Scinto

(57) ABSTRACT

A single flat panel detector provides radiation images which can correspond with various radiographic modes. In a radiation imaging apparatus including a flat panel detector which derives a radiation image according to incident radiation, a holding unit which holds the flat panel detector and a connecting mechanism capable of performing a connecting and a disconnecting between the holding unit and the flat panel detector, the flat panel detector can be controlled so that the maximum number of radiation images that the flat panel detector can derive when the flat panel detector is disengaged from the holding unit is smaller than the maximum number of radiation images that the flat panel detector can derive when the flat panel detector is held by the holding unit.

8 Claims, 8 Drawing Sheets

U.S. PATENT DOCUMENTS

| | | |
|---|---|---|
| 2003/0146390 A1 | 8/2003 | Vafi et al. ............... 250/370.15 |
| 2005/0109927 A1 | 5/2005 | Takenaka et al. .......... 250/252.1 |
| 2005/0121616 A1 | 6/2005 | Petrick .................. 250/370.09 |
| 2005/0199834 A1 | 9/2005 | Takenaka et al. ............ 250/580 |
| 2005/0200720 A1 | 9/2005 | Kameshima et al. ..... 348/220.1 |
| 2005/0220269 A1 | 10/2005 | Endo et al. ................... 378/114 |
| 2005/0264665 A1 | 12/2005 | Endo et al. ................... 348/308 |
| 2006/0119719 A1 | 6/2006 | Kameshima ................ 348/308 |
| 2006/0192130 A1 | 8/2006 | Yagi ...................... 250/370.14 |
| 2006/0289774 A1 | 12/2006 | Endo et al. ............. 250/370.09 |
| 2007/0040099 A1 | 2/2007 | Yokoyama et al. ....... 250/208.1 |
| 2007/0069144 A1 | 3/2007 | Kameshima ........... 250/370.09 |
| 2007/0080299 A1 | 4/2007 | Endo et al. ............. 250/370.09 |
| 2007/0096032 A1 | 5/2007 | Yagi et al. .............. 250/370.11 |
| 2007/0125952 A1 | 6/2007 | Endo et al. .................. 250/369 |
| 2007/0131843 A1 | 6/2007 | Yokoyama et al. .......... 250/205 |
| 2007/0183573 A1 | 8/2007 | Kameshima et al. ....... 378/98.9 |
| 2007/0210258 A1 | 9/2007 | Endo et al. ............. 250/370.09 |
| 2007/0290143 A1 | 12/2007 | Kameshima et al. ... 250/370.09 |
| 2007/0291904 A1 | 12/2007 | Takenaka et al. ............ 378/207 |
| 2007/0297567 A1 | 12/2007 | Takenaka et al. ........... 378/98.2 |
| 2008/0011958 A1 | 1/2008 | Endo et al. ............. 250/370.08 |
| 2008/0013686 A1 | 1/2008 | Kameshima et al. .......... 378/98 |
| 2008/0029688 A1 | 2/2008 | Yagi et al. ................ 250/208.1 |
| 2008/0054182 A1 | 3/2008 | Yokoyama et al. ..... 250/370.09 |
| 2008/0083876 A1 | 4/2008 | Endo et al. ................... 250/369 |

FOREIGN PATENT DOCUMENTS

| | | |
|---|---|---|
| EP | 1300695 A1 | 4/2003 |
| EP | 1537825 A1 | 6/2005 |
| JP | 11-009579 | 1/1999 |
| JP | 2000-037374 | 2/2000 |

RADIATION IMAGING APPARATUS

RELATED APPLICATIONS

This application is a divisional of patent application Ser. No. 11/814,749, filed Jul. 25, 2007, which is the U.S. national phase application of international patent application PCT/JP2007/051535, filed Jan. 24, 2007, claims benefit of the filing date of that application under 35 U.S.C. §120, and claims priority benefit under 35 U.S.C. §119 of Japanese patent applications nos. 2006-020975 and 2007-004676, filed Jan. 30, 2006, and Jan. 12, 2007, respectively. The entire contents of each of the mentioned prior domestic and foreign applications are incorporated herein by reference.

BACKGROUND OF THE INVENTION

Technical Field of the Invention

The present invention relates to a radiation imaging apparatus suited for use in medical diagnosis, for example, and in particular, to a radiation imaging apparatus including a flat panel detector using a semiconductor element as a detector. In the present invention, the term "radiation" includes not only α rays, β rays and γ rays which are beams of particles (including photons) emitted by radioactive decay, but also beams having energy higher than or comparable to that of those rays, for example, X-rays, particle beams, cosmic rays and others.

DESCRIPTION OF RELATED ART

Background Art

Hitherto, an image intensifier (hereinafter, abbreviated to I.I.) has been used as a detector for capturing radiation images in a radiation imaging apparatus for medical diagnosis for use in fluoroscopic radiography. The radiation imaging apparatus using I.I. performs fluoroscopic radiography in such a manner that radiation image information based on radiation that has passed through an object is converted into optical information and then the optical information is intensified in luminance, condensed and picked up by a camera.

With advances in thin-film semiconductor technology of late, a flat panel detector described in European Patent Publication No. 0791964 has been practically used as a detector for capturing radiation images. The flat panel detector has a converting unit in which a plurality of pixels consisting of thin film semiconductors are arrayed on an insulating substrate made of glass, and the converting unit converts radiation image information into an electrical signal to provide image information. The pixel has a converting element which converts radiation into an electric charge and a switching element which transfers the converted electric charge. Known converting elements include two types: an indirect-converting type composed of a scintillator which converts radiation into light and a photoelectric transducer which converts the converted light into an electric charge; and a direct-converting type using a semiconductor material which directly converts radiation into an electric charge. Known switching elements include: a thin film transistor (hereinafter, abbreviated to TFT) composed of a thin film semiconductor; and an element using a thin film diode or the like. The use of a non-single crystalline semiconductor such as an amorphous semiconductor or a polycrystalline semiconductor in the pixel composed of the thin film semiconductor enables realizing a detector which is larger in radiographic area and lighter in weight than that using a conventional I.I. FIG. 7 shows an example of the equivalent circuit for the flat panel detector.

Such a flat panel detector has been used as a detector for capturing still images such as X-raying using film until now. At present, use of a flat panel detector as a detector for radiographing moving images such as fluoroscopic radiography and the like has come to be a matter of interest and study. Japanese Patent Application Laid-Open No. H11-009579 discloses a radiation imaging apparatus using a flat panel detector as a detector. The radiation imaging apparatus uses a flat panel detector which is lighter in weight than and superior in portability to the conventional detector using an I.I. as a detector, so that the flat panel detector is detachably mounted. In addition, a plurality of flat panel detectors different in visual field size (or radiographing area) are prepared, to permit use of a flat panel detector suited for a demanded visual field size, thereby providing a single apparatus which can be operated with plural visual field sizes.

FIGS. 8A and 8B show an example of a radiation imaging apparatus using such a flat panel detector. FIG. 8A is a schematic diagram of a stationary radiation imaging apparatus to be used with the apparatus fixed to the ceiling of a consulting room. FIG. 8B is a schematic diagram of a mobile radiation imaging apparatus. In FIGS. 8A and 8B, reference numeral 801 denotes a radiation generating unit which generates radiation such as X-rays; 802, a flat panel detector; and 803, a holding unit called a "C-type arm" for holding the radiation generating unit 801 and the flat panel detector 802. Reference numeral 804 signifies a display unit capable of displaying radiation image information derived by the flat panel detector 802; and 805, a bed for placing thereon an object. In addition, reference numeral 806 indicates a carriage which can carry the radiation generating unit 801, the flat panel detector 802, the holding unit 803 and/or the display unit 804 and has a structure capable of controlling them; and 807, a fitting unit for fitting the radiation generating unit 801, the flat panel detector, and the holding unit 803.

DISCLOSURE OF THE INVENTION

As previously described, the radiation imaging apparatus using the flat panel detector has advantages over a conventional radiation imaging apparatus using I.I.; however it does not always sufficiently meet requirements in a medical site at present. In a medical site are performed plain radiography such as X-raying to derive still images and fluoroscopic radiography to derive moving images for fluoroscopic diagnosis. Since plain radiography aims to derive one image, it is possible to derive an image using a large amount of radiation. On the other hand, fluoroscopic radiography needs to derive plural images, so that the radiation dose per image used for capturing needs to be significantly smaller than that used in plain radiography. For this reason, a different operation control is required to make radiation image information derived by a very small radiation dose almost equal in quality to an image signal derived by plain radiography. Furthermore, a required radiographic area and radiation dose vary according to the radiographic properties different parts of the body, such as a head, chest and others. For this reason, an operation control varying according to radiographically different parts of the body is required. Japanese Patent Application Laid-Open No. H11-009579 discloses the radiation imaging apparatus in which a plurality of flat panel detectors corresponding to respective such radiographically different parts are prepared and detachably mounted. However, the preparation of a plurality of flat panel detectors for each such type of radiography may increase the cost of a radiation imaging apparatus and burden medical institutions with a heavy cost. Furthermore, operation controls suited for respective flat panel detectors are required, which may complicate the operation controls of the radiation imaging apparatus.

A radiation imaging apparatus of the present invention has a flat panel detector which derives a radiation image based on incident radiation, a holding unit which holds the flat panel detector and a connecting mechanism capable of performing a connecting and a disconnecting between the holding unit and the flat panel detector, where the connecting mechanism includes a mechanical connection unit which mechanically connects the flat panel detector to the holding unit and a heat transmitting unit which transmits heat between the flat panel detector and the holding unit.

Furthermore, a radiation imaging apparatus of the present invention includes a flat panel detector which derives a radiation image according to incident radiation, a holding unit which holds the flat panel detector and a connecting mechanism capable of performing a connecting and disconnecting between the holding unit and the flat panel detector, where the flat panel detector can be controlled so that the maximum number of images derived by a continuous radiography that the flat panel detector can perform in a state where the flat panel detector is disengaged from the holding unit is smaller than the maximum number of images derived by the continuous radiography that the flat panel detector can perform in a state where the flat panel detector is held by the holding unit.

Furthermore, a radiation imaging apparatus of the present invention includes a holding unit which holds a flat panel detector which derives a radiation image based on incident radiation, and a connecting mechanism capable of performing a connecting and a disconnecting between the holding unit and the flat panel detector, where the connecting mechanism includes a mechanical connection unit which mechanically connects the flat panel detector to the holding unit and a heat transmitting unit which transmits heat between the flat panel detector and the holding unit.

The present invention enables performing plain radiography and short-time fluoroscopic radiography with a flat panel detector removed from the holding unit and providing the radiation imaging apparatus capable of handling various radiographic modes with portability, which is a feature of the flat panel detector, maintained. In addition, various radiographic modes can be handled by a single flat panel detector, which can suppress increase in cost of the radiation imaging apparatus and burden to medical institutions with cost.

Further features of the present invention will become apparent from the following description of exemplary embodiments with reference to the attached drawings.

BEST MODE FOR CARRYING OUT THE INVENTION

The preferred mode for carrying out the invention is described below with reference to the drawings. Since the flat panel detector used in the radiation imaging apparatus of the present invention can be represented by the same equivalent circuit as in the conventional one, the flat panel detector is described by using FIG. 7.

Figure 7:
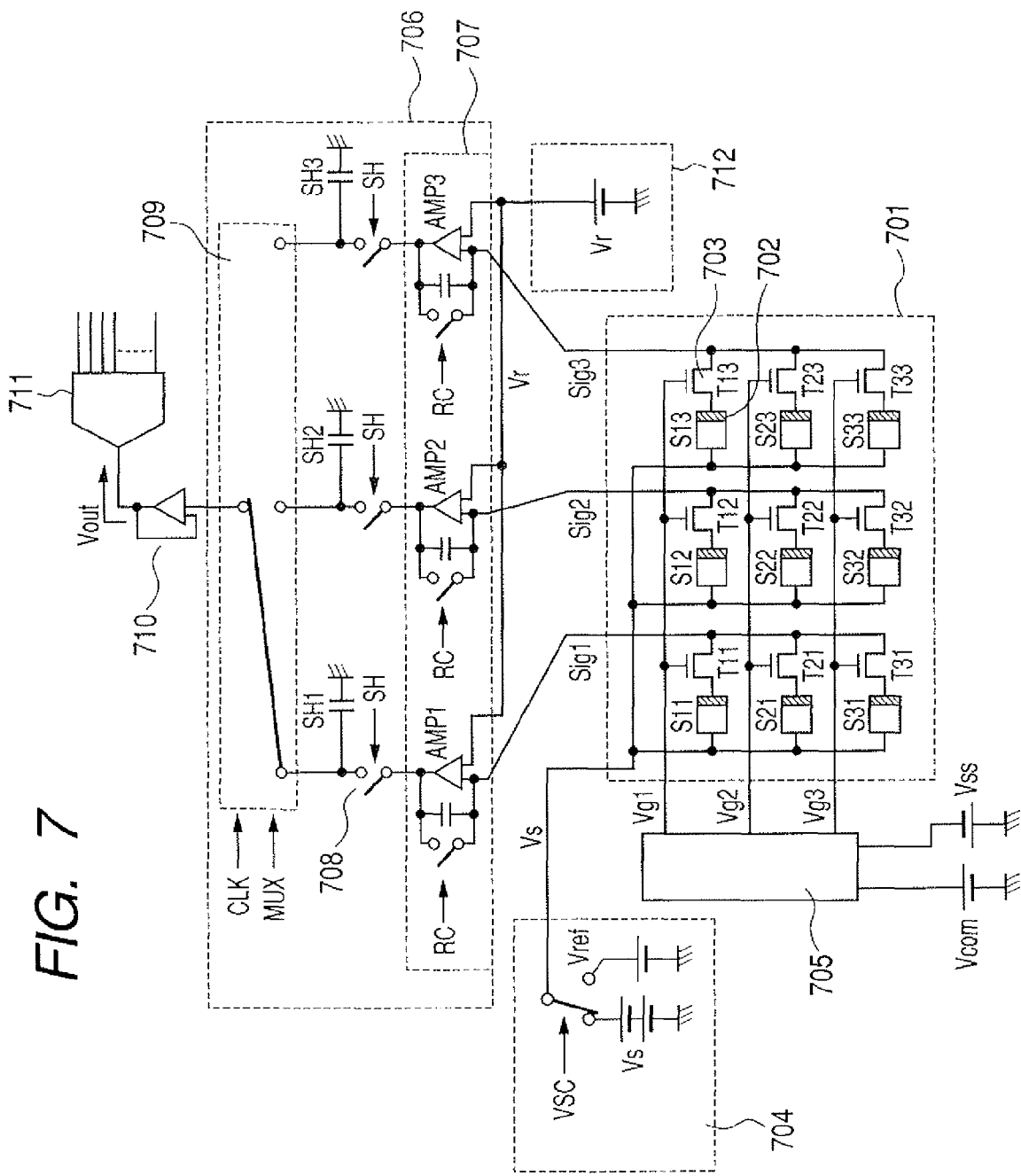
FIG. 7 is an equivalent circuit of the flat panel detector.
Figure 8A:
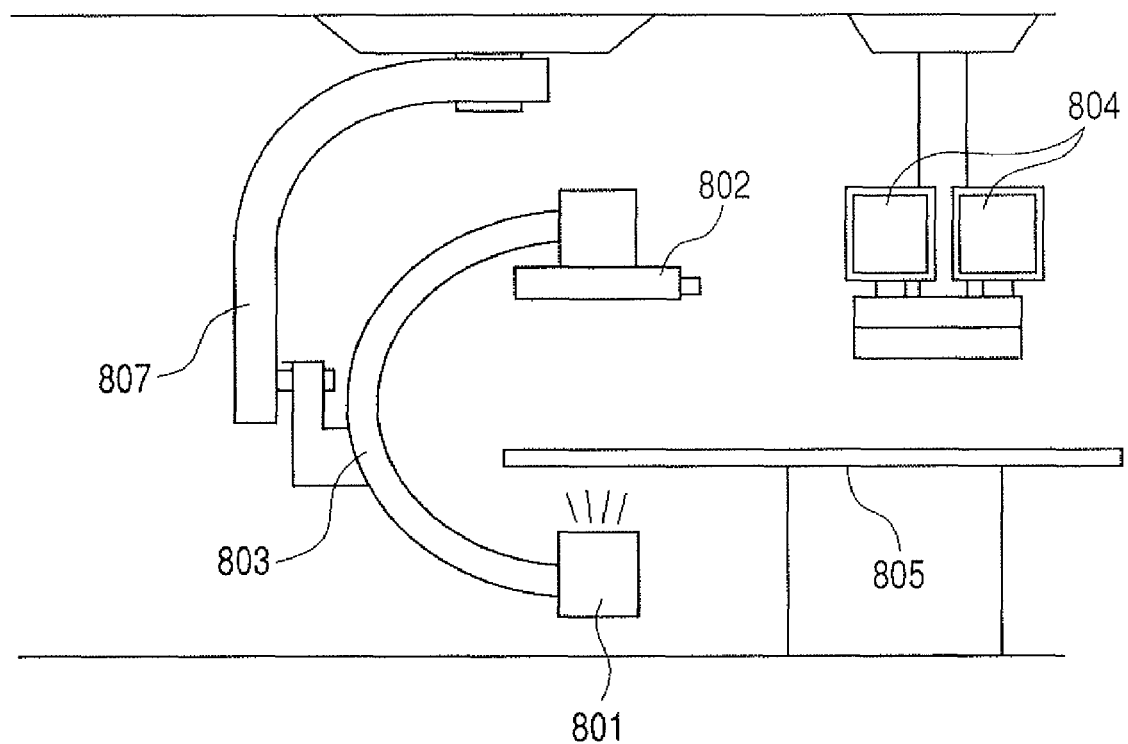
FIGS. 8A and 8B are schematic views illustrating a conventional radiation imaging apparatus.
Figure 8B:
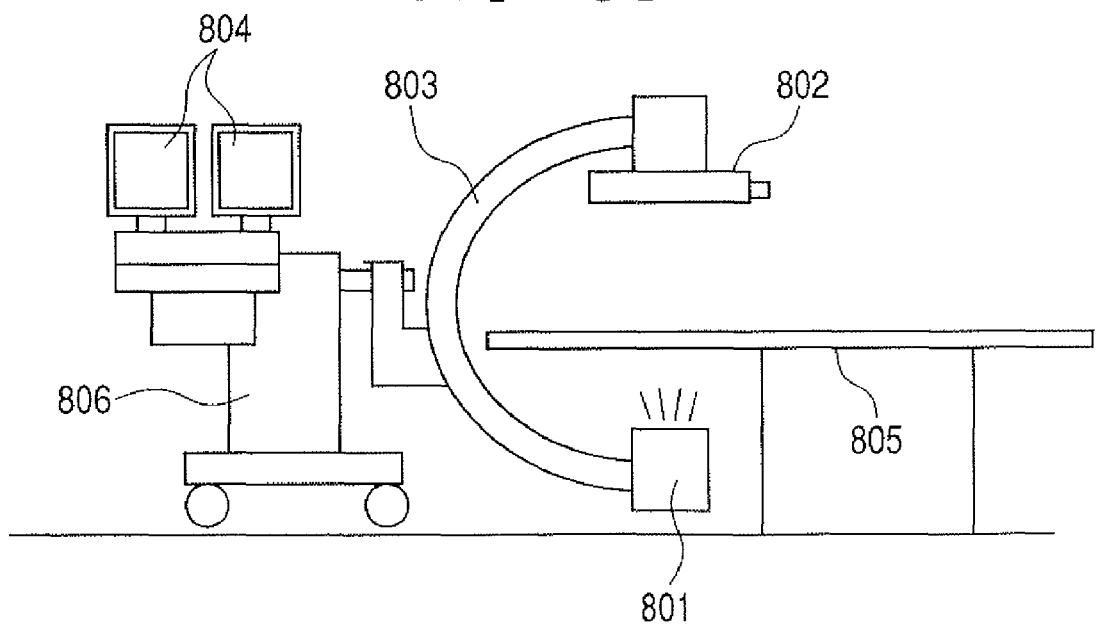

In FIG. 7, reference numeral 701 denotes a converting unit; 702, a converting element which converts radiation into electric charge; and 703, a switching element which transfers the electric charge converted by the converting element 702. The following two types are preferably used for the converting elements 702: an indirect-converting type composed of a scintillator which converts radiation into light and a photoelectric transducer which converts the converted light into an electric charge; and a direct-converting type using a semiconductor material which directly converts radiation into an electric charge. A TFT composed of a thin film transistor or thin film diode is preferably used as the switching element 703. In FIG. 7, a scintillator (not shown) and a MIS photoelectric transducer are used as the converting element 702 and a TFT is used as the switching element 703. The present invention does not limit the converting element 702 to the MIS photoelectric transducer, but other photoelectric transducers such as, for example, a PIN photodiode or the like is applicable. A plurality of converting elements 702 of S11 to S33 are arranged. A plurality of switching elements 703 of T11 to T33 are also arranged. A pair of the converting element 702 and the switching element 703, for example, a pair of S11 and T11, forms one pixel. A plurality of such pixels are arrayed to form the converting unit 701. A driving wiring Vg1 is commonly connected to the control electrodes of a plurality of the switching elements T11 to T13 in a row direction. A driving wiring Vg2 is commonly connected to the control electrodes of a plurality of the switching elements T21 to T23 in a row direction. A driving wiring Vg3 is commonly connected to the control electrodes of a plurality of the switching elements T31 to T33 in a row direction. The driving wirings VG1 to Vg3 are connected to a driving circuit 705 for driving and controlling the switching elements T11 to T33 for pixels. The driving circuit 705 provides the driving wirings Vg1 to Vg3 with driving signals to allow a row-based driving control. In addition, a signal wiring Sig1 is commonly connected to one of the source and the drain electrode of a plurality of the switching elements T11 to T31 in a column direction. Similarly, a signal wiring Sig2 is commonly connected to one of the source and the drain electrode of a plurality of the switching elements T12 to T32 in a column direction, and a signal wiring Sig3 is commonly connected to one of the source and the drain electrode of a plurality of the switching elements T13 to T33 in a column direction. The signal wirings Sig1 to Sig3 are connected to a signal processing circuit 706 for reading analog signals based on electric charges converted by the converting element 702 and transferred by the switching element. The signal processing circuit 706 includes an amplifying unit 707 composed of amplifiers AMP 1 to AMP 3 provided corresponding to the signal wirings Sig1 to Sig3 respectively. The signal processing circuit 706 further includes sample hold units 708 composed of SH 1 to SH 3 which temporarily hold respective outputs of AMP 1 to AMP 3. The signal processing circuit 706 still further includes a multiplexer 709 which converts a parallel signal from the sample hold unit 708 (SH 1 to SH 3) into a series signal. Reference numeral 710 denotes an amplifier provided at the rear stage of the signal processing circuit 706; and 711, an A/D converter which converts an analog electric signal from the signal processing circuit 706 into a digital signal. Reference numeral 712 indicates a reference power supply unit for providing the signal processing circuit 706 with reference electric potential; and 704, a power supply unit for providing bias to a bias wiring Vs commonly connected to one electrode of respective converting elements S11 to S33. The other electrode of respective converting elements S11 to S33 is connected to the other of the source and the drain electrode of respective switching elements T11 to T33.

In the next place, the operation of the flat panel detector is described using FIG. 7. First, the reference power supply unit 712 provides a reference electric potential to the signal wiring to reset the signal wirings Sig1 to Sig3, and then the power supply unit 704 provides a bias to the converting elements S11 to S33 to enable them to perform the converting operation. Next, radiation is caused to be incident on the converting unit 701 with the switching elements T13 to T33 in the non-conducting state and the converting elements S11 to S33 convert radiation into an electric charge according to the incident radiation. The driving operation described below is conducted to read the converted electrical charges for each row from the converting unit 701. First, the driving circuit 705 provides a driving signal to the driving wiring Vg1 on a first row to bring the switching elements T11 to T13 connected to the driving wiring Vg1 on the first row into conduction. The switching elements T11 to T13 in the conducting state transfer the electrical charges converted by converting elements S11 to S13 to the signal wirings Sig1 to Sig3 respectively. The transferred electric charges are transmitted in parallel to the signal processing circuit 706, amplified by the amplifiers AMP 1 to AMP 3 connected to the signal wirings Sig1 to Sig3 respectively and outputted in parallel as analog signals. The outputted analog signals are stored in parallel in the sample hold circuits SH 1 to SH 3 provided at the rear stage of the amplifiers AMP 1 to AMP 3. Parallel analog electrical signals from the sample hold circuits SH 1 to SH 3 are converted into series signals by the multiplexer 709. The converted series signals are inputted into the A/D converter 711 through the amplifier 710 to perform an analog-to-digital conversion, and outputted as one row of digital signal. After the analog electric signals on the first-row have been outputted from the amplifiers AMP 1 to AMP 3 and stored in the sample hold circuits SH1 to SH 3, the signal wirings Sig1 to Sig3 are reset for the transfer of the following row and then the electric charges on the second row are transferred as is the case with those on the first row. Such a driving operation enables conversion to a series signal and conversion from analog to digital signal on the first row and transfer operation on the second row at the same period. Such a driving operation from the first to the third row produces one image of radiation images or a plain radiation image. Repeating such a driving operation required for one image produces plural images of radiation images, and sequentially producing plural images of radiation images produces fluoroscopic images.

Thus, a medical site requires plural radiographic modes such as plain radiography and fluoroscopic radiography using a single radiation imaging apparatus with a flat panel detector. However, plain radiography is different from fluoroscopic radiography in the required operation control of a flat panel detector. The fluoroscopic radiography needs to produce plural images of radiation images, so that the dose of radiation delivered to an object to produce a single radiation image needs to be significantly smaller than that used in plain radiography. The dose of radiation delivered to an object to produce one radiation image in fluoroscopic radiography is 1 to 3 orders of magnitude lower than that in plain radiography, although the exact ratio depends on the number of radiation images to be used for fluoroscopic radiography. However, one radiation image whether produced in plain radiography or in fluoroscopic radiography is required to be the same in quality, so that operation control needs to be changed related in particular to the signal processing circuit of the flat panel detector. In other words, the amplification factor of the signal processing circuit in fluoroscopic radiography requires further increasing than that in plain radiography, or the sensitivity of the pixel requires increasing. For that reason, the signal processing circuit and the flat panel detector as a whole in fluoroscopic radiography consume more power than those in plain radiography, which leads to an increase in the heat quantity produced by the signal processing circuit and the flat panel detector as a whole. Furthermore, fluoroscopic radiography typically takes more time than plain radiography, which leads to an increase in consumption of power by the signal processing circuit and the flat panel detector as a whole and in the resulting heat quantity produced, as well. As described earlier, the pixel used in the flat panel detector is composed of semiconductors, so that an increase in temperature causes dark current and leakage current to increase, which may generate an artifact on radiation images. Furthermore, the signal processing circuit of the flat panel detector is also composed of semiconductors, so that, again, a rise in temperature increases noise and causes variation in characteristics, which may generate an artifact on radiation images. When a radiation image is used for a medical diagnosis, those artifacts may result in degradation in picture quality of the radiation image.

Consideration has been made to provide the flat panel detector with a water cooling mechanism which cools the detector by liquid using a heat pipe and an air cooling mechanism which cools the detector by air using a fan in order to suppress rise in temperature of the flat panel detector. However, it is important that the flat panel detector can be carried (hereinafter referred to as its "portability"). Providing the abovementioned cooling mechanism increases the weight of the flat panel detector, degrading portability. In addition, if the flat panel detector increases in weight, it becomes difficult to attach the detector to or detach the detector from the C-type arm used as the holding unit, and in addition, the holding unit requires an increase in its mechanical strength.

In the present invention, the radiation imaging apparatus of which the flat panel detector is detachably mounted on the holding unit is configured as described in the following.

When the maximum number of images derived by a radiography that the flat panel detector can perform at a state that the flat panel detector is removed from the holding unit is "n", and when the maximum number of images derived by the radiography that the flat panel detector can perform at a state that the flat panel detector is held by the holding unit is "m", the flat panel detector is so controlled that m is greater than n (m>n). The flat panel detector is provided with a heat radiator for radiating generated heat to the outside. When continuous radiography is performed at a state that the flat panel detector is removed from the holding unit, the maximum number of images of radiography that the flat panel detector can perform needs to be restricted. The reason is that the heat radiator requires suppressing rise in temperature caused by heat in capturing to a temperature at which the flat panel detector is not adversely affected. That is to say, when the flat panel detector derives images in a state in which the flat panel detector is removed from the holding unit, it is important to restrict the number of images derived by the continuous radiography to a number equal to or smaller than the maximum number of images consistent with the heat radiator suppressing a rise in temperature to a prescribed temperature.

In a conversion unit 701 having pixels formed from a thin film semiconductor such as amorphous silicon, as the temperature rises, dark current will increase. Due to the dark current, a noise component contained in the image signal increases. Thus, the S/N ratio will be degraded. When the conversion unit 701 formed from a thin film semiconductor is maintained at a temperature equal to or lower than 50° C., a satisfactory S/N ratio required in a radiation imaging apparatus can be secured. Accordingly, in a state in which the flat panel detector is removed from the holding unit, it is desirable to set the maximum number n of the images so that the conversion unit 701 is maintained at a temperature equal to or lower than 50° C. In a signal processing circuit 706 and A/D converter 711, as the temperature rises, power consumption and dark current increase. Thus, again, the S/N ratio will be degraded. A temperature at which the signal processing circuit 706 and the A/D converter 711 can operate normally is approximately equal to or lower than 70° C. Accordingly, in a state in which the flat panel detector is removed from the holding unit, it is desirable to set the maximum number n of the images so that the signal processing circuit 706 and the A/D converter 711 are maintained at a temperature equal to or lower than 70° C. It should also be noted that continuous radiography involves radiographing with the flat panel detector without turning off a power source thereof, and includes plural times of still image radiography and moving image fluoroscopy without turning off a power source thereof.

On the other hand, the radiation imaging apparatus is equipped with a cooling mechanism separately from the flat panel detector, and the cooling mechanism cools the flat panel detector through the holding unit with the flat panel detector attached to the holding unit. The cooling mechanism may be provided in the holding unit or may be provided on a carriage or a fitting unit. In addition, the holding unit and/or the flat panel detector is provided with a connecting mechanism which mechanically connects the flat panel detector. The connecting mechanism is provided with a mechanical connecting unit which performs a mechanical connection with the flat panel detector, an electric connecting unit which performs an electric connection with the flat panel detector and a thermal connecting unit which thermally connects the heat radiator of the flat panel detector to the cooling mechanism to transfer the heat generated in the flat panel detector. Cooling heat generated in the flat panel detector by the cooling mechanism through the heat radiator and the thermal connecting unit enables the unit to capture more radiation images with the flat panel detector attached to the holding unit than can be done with the flat panel detector removed from the holding unit.

This allows performing plain radiography and short-time fluoroscopic radiography with the flat panel detector removed from the holding unit and providing the radiation imaging apparatus capable of handling various radiographic modes with portability, which is a feature of the flat panel detector, maintained. In addition, various radiographic modes can be handled by a single flat panel detector, which avoids an increase in cost of the radiation imaging apparatus and burden to medical institutions with cost.

The embodiments of the present invention are described in detail below with reference to the drawings.

First Embodiment

Figure 1A:
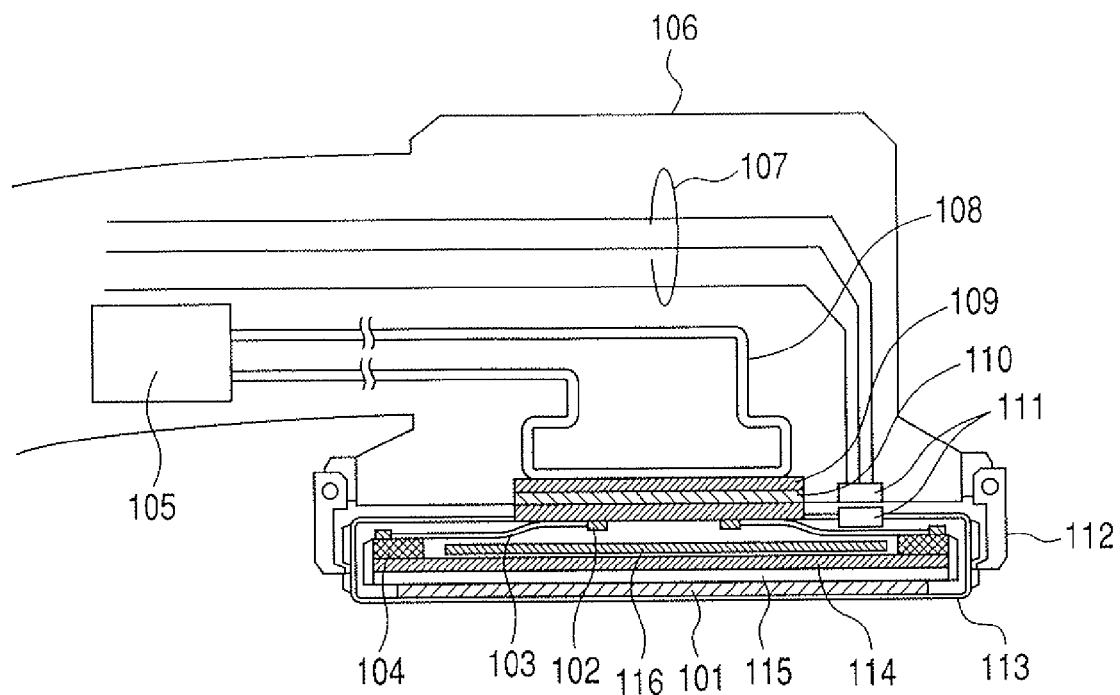
FIG. 1A is a cross-section of a flat panel detector and a holding unit illustrated with the flat panel detector fixed to the holding unit in a radiation imaging apparatus according to a first embodiment of the present invention.
Figure 1B:
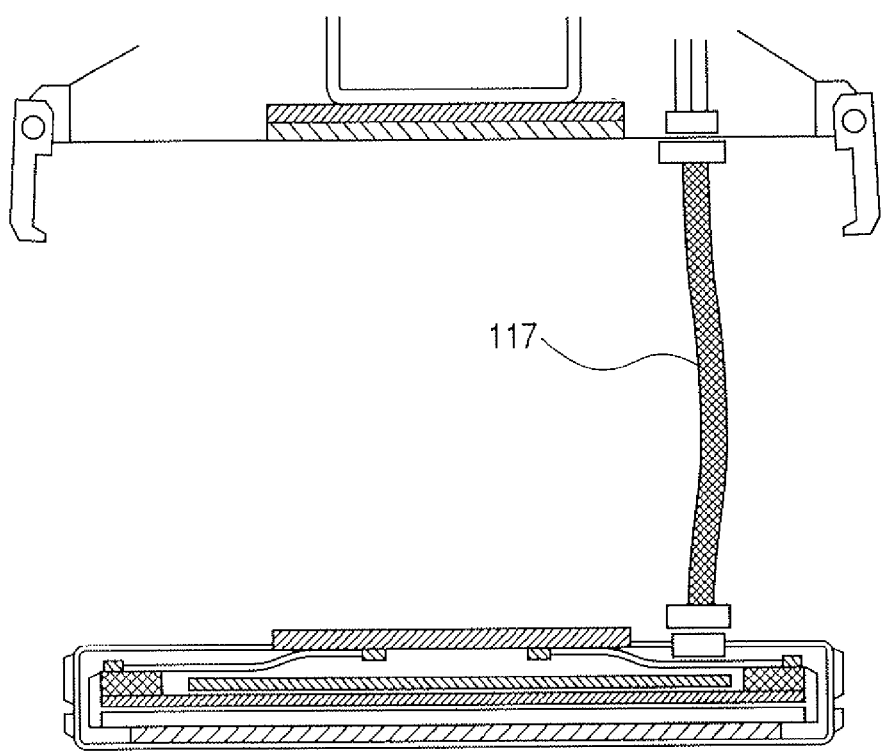
FIG. 1B is a cross-section of the flat panel detector and the holding unit illustrated with the flat panel detector removed from the holding unit in the radiation imaging apparatus according to the first embodiment of the present invention.

The first embodiment of the present invention is described in detail with reference to FIGS. 1A and 1B. FIGS. 1A and 1B are enlarged cross-sections of a flat panel detector and a holding unit in the radiation imaging apparatus of the present invention. FIG. 1A is a cross-section illustrated with the flat panel detector fixed to the holding unit. FIG. 1B is a cross-section illustrated with the flat panel detector removed from the holding unit.

In FIGS. 1A and 1B, reference numeral 101 denotes a scintillator; 102, a first thermal diffusion plate; 103, a first heat pipe; 104, a signal processing circuit; 105, a cooling mechanism; 106, a C-type arm being a holding unit; 107, an electric wiring; 108, a second heat pipe; and 109, a second thermal diffusion plate. Reference numeral 110 indicates a thermal conduction plate; 111, a connector being an electric connecting unit; 112, a fixing hook being a mechanical connecting unit; 113, a housing; 114, a support base; 115, a sensor panel; 116, a circuit board; and 117, a cable.

The flat panel detector of the present embodiment is composed of the scintillator 101, the first thermal diffusion plate 102, the first heat pipe 103, the signal processing circuit 104, the connector 111, the housing 113, the support base 114, the sensor panel 115 and the circuit board 116. The sensor panel 115 has such a structure that a plurality of pixels including photoelectric transducers and TFTs are arranged in two dimensions on an insulating substrate such as glass, and driving wirings, signal wirings and bias wirings are provided. The sensor panel 115 has a configuration illustrated in the equivalent circuit in broken line in FIG. 7. The scintillator 101 is arranged on the incoming side of radiation on the sensor panel 115 and converts the incident radiation into light in a wavelength range which the photoelectric transducers in the sensor panel 115 can detect. In the present embodiment, the converting element 702 in FIG. 7 is composed of the photoelectric transducer and the scintillator corresponding thereto. The signal processing circuit 104 reads a radiation image signal from the sensor panel 115 and is a semiconductor circuit composed of the amplifier 707, the sample hold unit 708 and multiplexer 709 in FIG. 7. The circuit board 116 has an integrated circuit with the amplifier 710 and the A/D converter 711 in FIG. 7, a signal processing circuit which processes the read signal, a control circuit which controls a driving circuit (not shown) and the signal processing circuit 104 and a power supply circuit. The connector 111 electrically connects the flat panel detector to the electric wiring 107 provided on the C-type arm 106. The first heat pipe 103 conducts heat generated in the signal processing circuit 104 to the first thermal diffusion plate 102 and is disposed in contact with the first thermal diffusion plate 102. The term heat pipe is a generic term for a heat conduction system utilizing phase change such as vaporization/liquefaction of liquid sealed inside and capillarity. The heat pipe is very high in heat conductivity and efficiently conducts heat. The heat pipe has a higher degree of freedom in shape, has no movable part and is maintenance-free, which is suited for apparatus requiring high reliability such as medical equipment. The thermal diffusion plate 102 is a member for radiating heat conducted from the first heat pipe 103 to the outside of the flat panel detector. In FIG. 1A, the thermal diffusion plate 102 conducts heat in contact with the thermal conduction plate 110 provided on the C-type arm 106. As show in FIG. 1B, the first thermal diffusion plate 102 radiates heat generated in the flat panel detector outside by natural heat radiation with the flat panel detector removed from the C-type arm. In other words, in the present embodiment, the first heat pipe 103 and the first thermal diffusion plate 102 form a heat radiator. It is preferable to use metal high in heat conductivity such as copper or aluminum as a material of the first thermal diffusion plate 102. The support base 114 supports the sensor panel 115, circuit board 116 and the signal processing circuit. The housing 113 is a container which holds the scintillator 101, the first thermal diffusion plate 102, the first heat pipe 103, the signal processing circuit 104, the connector 111, the support base 114, the sensor panel 115 and the circuit board 116 in its inside.

On the other hand, the C-type arm 106 is composed of the cooling mechanism 105, the electric wiring 107, the second heat pipe 108, the second thermal diffusion plate 109, the thermal conduction plate 110, the connector 111 and the fixing hook 112. The thermal conduction plate 110 serves to conduct heat conducted from the first thermal diffusion plate 102 of the flat panel detector to the second thermal diffusion plate 109 provided on the C-type arm 106. It is preferable to use a sheet material using silicone rubber or acrylic rubber high in heat conductivity as a material for the thermal conduction plate 110. Connecting the metallic thermal diffusion plates with each other precludes heat from being efficiently conducted because of air space produced between the plates, which can be prevented by the above sheet material. The second thermal diffusion plate 109 conducts heat conducted through the thermal conduction plate 110 to the second heat pipe 108. It is preferable that the second thermal diffusion plate 109 uses the same material as the first thermal diffusion plate 102. The second heat pipe 108 conducts heat conducted from the second thermal diffusion plate 109 to the cooling mechanism 105 for cooling it. It is preferable that the second heat pipe 108 uses the same material as the first heat pipe 103. The cooling mechanism 105 cools heat conducted by the second heat pipe 108. In the present embodiment, the second heat pipe 108, the second thermal diffusion plate 109 and the thermal conduction plate 110 form a thermal connecting unit. The electric wiring 107 supplies the flat panel detector with a power source and an electric signal required to drive it through the connector 111 from the C-type arm 106 and transmits a radiation image signal from the flat panel detector and a system-status signal to the C-type arm 106. The fixing hook 112 mechanically holds the flat panel detector in the C-type arm and functions as a mechanical connecting unit. On the sides of the housing 113 of the flat panel detector are formed grooves which are caught on the fixing hook 112 to fix the flat panel detector to the C-type arm.

In the present embodiment, the first heat pipe 103 and the first thermal diffusion plate 102, which are a heat radiator, conduct heat generated in the signal processing circuit 104 of the flat panel detector to the cooling mechanism 105 through the thermal conduction plate 110, the second thermal diffusion plate 109 and the second heat pipe 108, which are a thermal connecting unit, for cooling it with the flat panel detector fixed to the C-type arm. In addition, the first thermal diffusion plate 102 radiates heat generated in the flat panel detector outside by natural heat radiation with the flat panel detector removed from the C-type arm. Thus, capturing images with the flat panel detector fixed to the C-type arm 106 enables capturing more radiation images than that with the flat panel detector removed from the C-type arm 106.

In the present embodiment, a cable extension 117 is used for electrical connection when the flat panel detector is removed from the C-type arm 106. However, the present invention is not limited to the cable extension, but a known radio communication may be used to transmit and receive radiation image data, and the flat panel detector may be provided with a separate power supply.

Second Embodiment

Figure 2A:
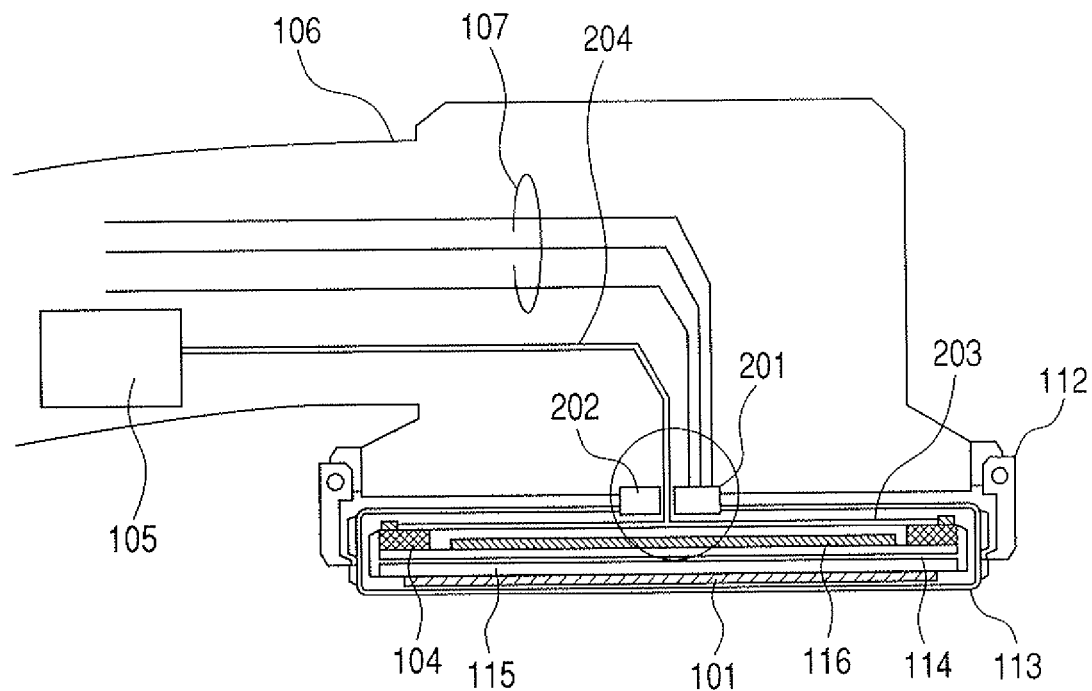
FIG. 2A is a cross-section of a flat panel detector and a holding unit illustrated with the flat panel detector fixed to the holding unit in a radiation imaging apparatus according to a second embodiment of the present invention.
Figure 2B:
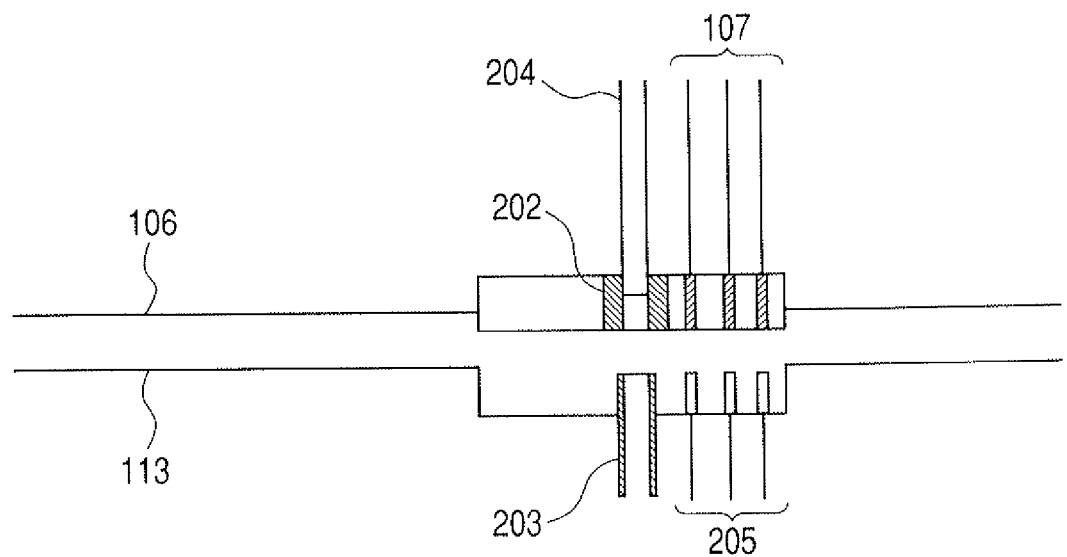
FIG. 2B is a cross-section of the flat panel detector and the holding unit illustrated with the flat panel detector removed from the holding unit in the radiation imaging apparatus according to the second embodiment of the present invention.

The second embodiment of the present invention is described in detail with reference to FIGS. 2A and 2B. FIGS. 2A and 2B are enlarged cross-sections of a flat panel detector and a holding unit in the radiation imaging apparatus of the present invention. FIG. 2A is a cross section illustrated with the flat panel detector fixed to the holding unit. FIG. 2B is a cross-section illustrated with the flat panel detector removed from the holding unit. Incidentally, the same reference numerals are used for the same composing elements as in the first embodiment to omit the detailed descriptions thereof.

Reference numeral 201 represents a connector electrically connecting the flat panel detector to the electric wiring 107 provided on the C-type arm 106. Reference numeral 202 denotes a fitting of metal such as copper high in heat conductivity which is so configured as to bring a first heat pipe 203 into contact with a second heat pipe 204 to conduct heat from the first heat pipe 203 to the second heat pipe 204. Reference numeral 203 designates a first heat pipe to conduct heat generated in the signal processing circuit 104 to the fitting 202. Reference numeral 204 represents a second heat pipe to conduct heat conducted from the first heat pipe 203 through the fitting 202 to the cooling mechanism 105 to cool it. Reference numeral 205 denotes an electric connecting unit of the flat panel detector.

In the present embodiment, the fitting 202 conducts heat between the first heat pipe 203 and the second heat pipe 204 instead of the first thermal diffusion plate 102, the thermal conduction plate 110 and the second thermal diffusion plate 109. In the present embodiment, the first heat pipe 203 is provided as a heat radiator, and the fitting 202 and the second heat pipe 204 are provided as a thermal connecting unit.

In the present embodiment, a heating portion is not exposed to the surface of the housing 113 of the flat panel detector, so that the heating portion is not exposed when the flat panel detector is removed from the C-type arm 106, which enhances safety, in addition to the same effect as in the first embodiment. The apparatus in the present embodiment further decreases in weight by the amount corresponding to the weight of the thermal diffusion plate than that in the first embodiment, which improves portability.

Third Embodiment

Figure 3:
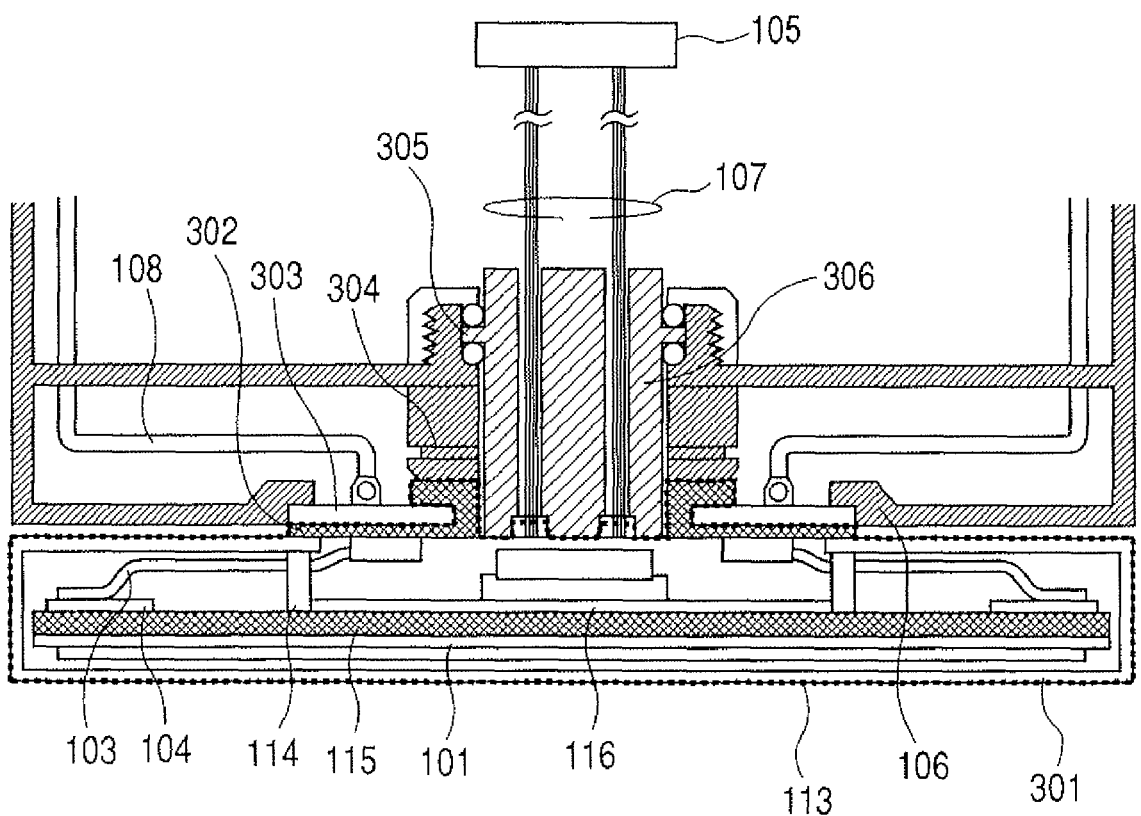
FIG. 3 is a cross-section of a flat panel detector and a holding unit illustrated with the flat panel detector fixed to the holding unit in a radiation imaging apparatus according to a third embodiment of the present invention.
Figure 4A:
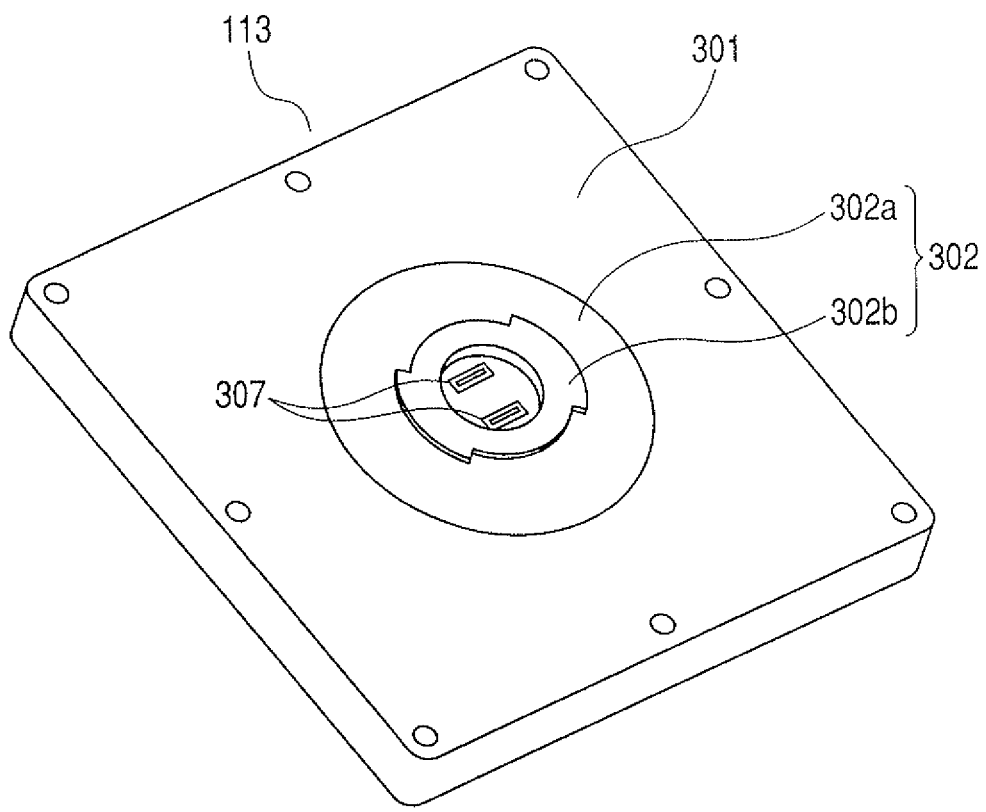
FIG. 4A is a schematic perspective view illustrating the connecting mechanism of the flat panel detector.
Figure 4B:
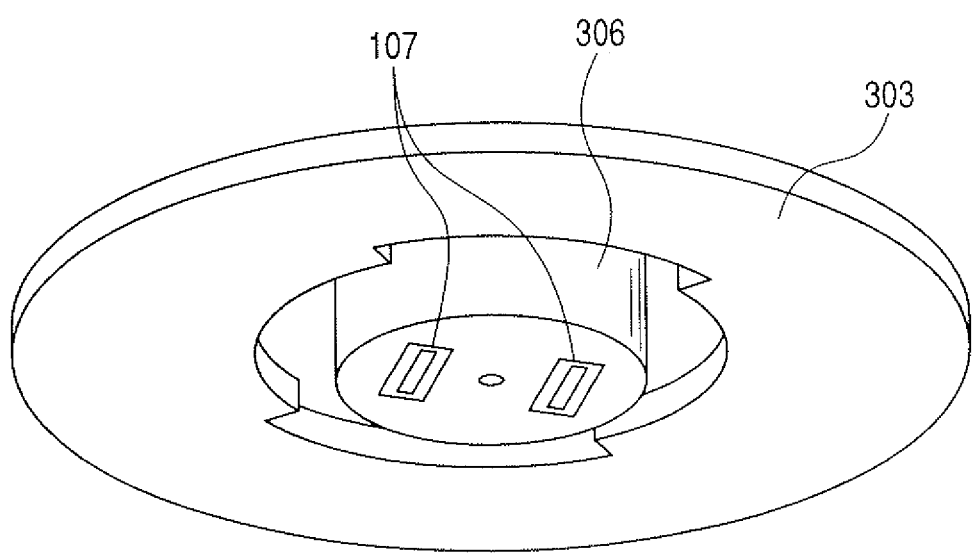
FIG. 4B is a schematic perspective view illustrating the connecting mechanism of the holding unit.
Figure 5A:
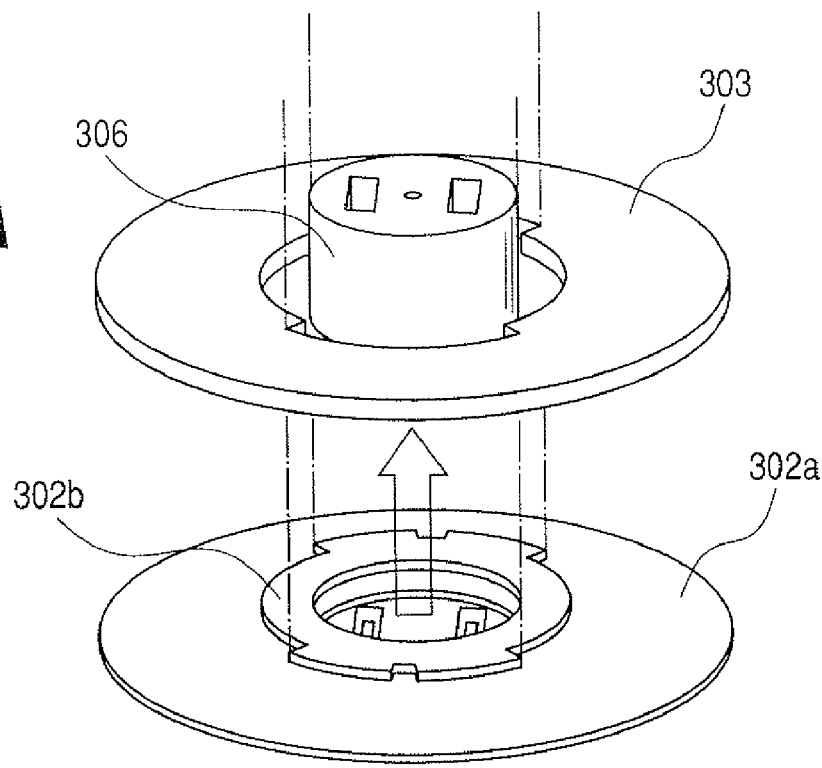
FIGS. 5A, 5B and 5C are schematic perspective views illustrating a method of connecting the flat panel detector to the holding unit in the radiation imaging apparatus according to the third embodiment of the present invention.
Figure 5B:
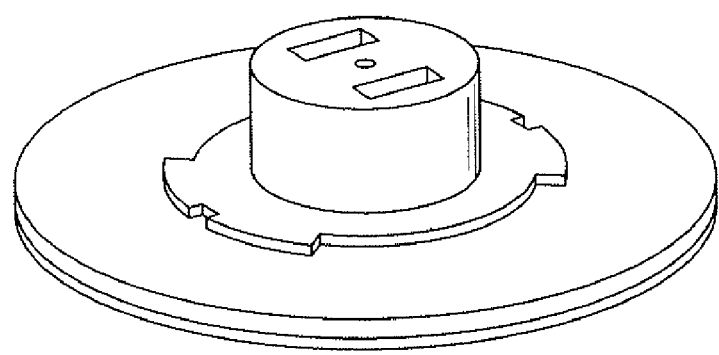
Figure 5C:
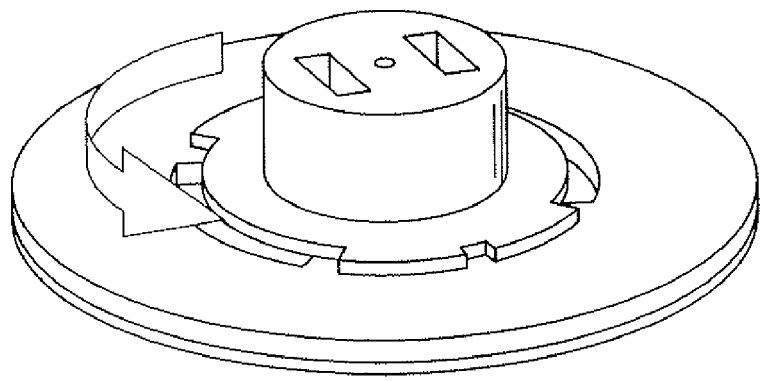

The third embodiment of the present invention is described in detail with reference to FIGS. 3 to 5C. FIG. 3 is a cross section illustrated with the flat panel detector fixed to the holding unit. FIG. 4A is a schematic perspective view illustrating the connecting mechanism of the flat panel detector and FIG. 4B is a schematic perspective view illustrating the connecting mechanism of the holding unit. FIGS. 5A, 5B and 5C are schematic perspective views illustrating a method of connecting the flat panel detector to the holding unit. Incidentally, the same reference numerals are used for the same composing elements as in the first or the second embodiment to omit the detailed descriptions thereof.

In the present embodiment, mechanical, electric and thermal connections are made using a first connecting mechanism provided on the flat panel detector and a second connecting mechanism provided on the C-type arm 106 that serves as a holding unit. Reference numeral 301 denotes a flat panel detector of the present embodiment and includes the scintillator 101, the first heat pipe 103, the signal processing circuit 104, the housing 113, the support base 114, the sensor panel 115, the circuit board 116, a first connecting mechanism 302 and a connector 307. Reference numeral 302 signifies a first connecting mechanism to radiate heat conducted from the first heat pipe 103 to the outside of the flat panel detector 301 and to make connection of the flat panel detector 301 to the second connecting mechanism of the C-type arm 106 to conduct heat. The first connecting mechanism 302 has a heat radiating member 302a for radiating heat outside or conducting heat to the second connecting unit and a fixing member 302b for mechanically connecting the flat panel detector 301 to the second connecting mechanism of the C-type arm 106. A flange including a metallic part high in heat conductivity is preferably used for the first connecting mechanism 302. Reference numeral 303 denotes a heat conducting member to conduct heat from the heat radiating member 302a to the cooling mechanism 105 through the second heat pipe 108. A flange including a metallic part high in heat conductivity is preferably used for the heat conducting member 303 as is the case with the heat radiating member 302a. Reference numeral 304 represents a fixing member for fixing the first connecting mechanism 302, for example, by inserting a pin into a notch provided in the first connecting mechanism 302 or by forcibly pressing the first connecting mechanism 302 downward. Reference numeral 305 indicates a bearing to rotatably support a wiring connecting unit 306. Reference numeral 306 indicates a wiring connecting unit which is cylindrical and includes an electric wiring 107 therein. Reference numeral 307 denotes a connector of the flat panel detector 301 which makes electrical connection with the electric wiring 107. In the present embodiment, the second connecting mechanism of the C-type arm 106 includes the heat conducting member 303, the fixing member 304, the bearing 305 and the wiring connecting unit 306. The heat conducting member 303 and the second heat pipe 108 form a thermal connecting unit.

In the next place, a method of fixing the flat panel detector 301 to the C-type arm 106 of the present invention is described using FIGS. 5A to 5C. First, as shown in FIG. 5A, the protrusions provided on the first connecting mechanism 302 of the flat panel detector 301 are mated with notches provided on the heat conducting member 303 of the C-type arm 106. As shown in FIG. 5B, the flat panel detector 301 is pressed into the C-type arm 106 with the protrusions mated with the notches. At this point, the fixing member 302b is positioned inside the heat conducting member 303. Furthermore, the wiring connecting unit 306 of the C-type arm 106 is connected to the connector 307 of the flat panel detector 301 to establish an electrical connection. As shown in FIG. 5C, with the flat panel detector 301 pressed into the C-type arm 106, the flat panel detector 301 is rotated by a predetermined angle to complete fixing.

(Application)

Figure 6A:
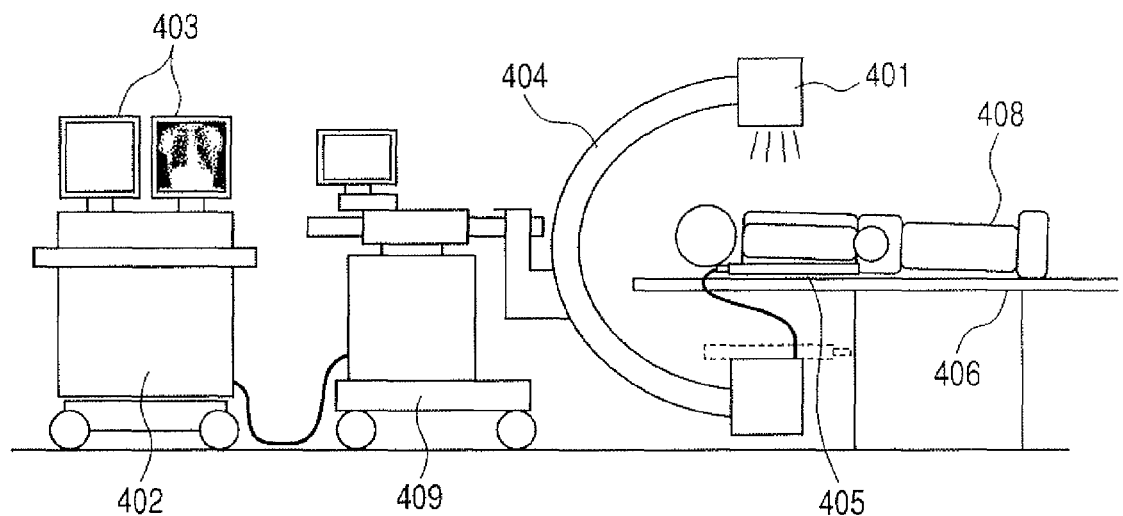
FIGS. 6A and 6B are schematic views illustrating an application of the radiation imaging apparatus of the present invention.
Figure 6B:
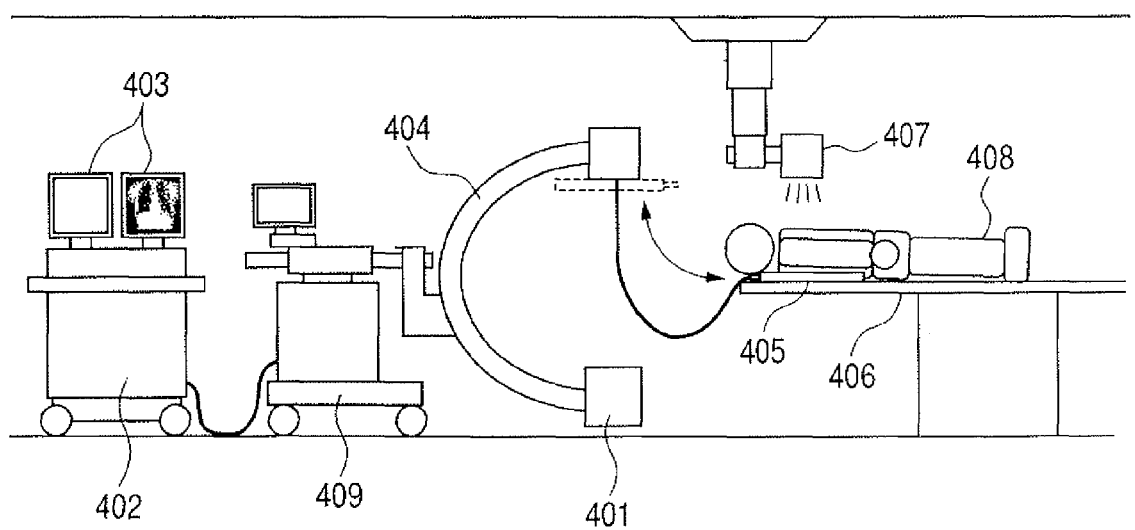

FIGS. 6A and 6B illustrate an application of a mobile radiation imaging apparatus using the present invention. FIG. 6A is an example showing a case where radiography is conducted using a radiation source 401 provided on the C-type arm with the flat panel detector removed from the C-type arm, in a mobile radiation imaging apparatus capable of performing fluoroscopic radiography and still image photography. Here, reference numeral 401 denotes a radiation generating unit; 405, a flat panel detector; 404, a C-type arm for holding the radiation generating unit 401 and the flat panel detector 405. Reference numeral 403 represents a display unit capable of displaying radiation image information derived by the flat panel detector 405; and 406, a bed for placing thereon an object 408. Reference numeral 409 denotes a carriage capable of carrying the radiation generating unit 401, the flat panel detector 405 and the C-type arm 404; and 402, a mobile system capable of controlling those. In this application, the flat panel detector 405 is capable of deriving images within the maximum number of images of radiation images "n" consistent with the heat radiator described in the above embodiment suppressing a rise in temperature to a temperature at which the flat panel detector is not adversely affected, for example, the flat panel detector 405 can perform a still image photography and a short-time fluoroscopic radiography. In addition, with the flat panel detector 405 fixed to the C-type arm 404, heat generated in the flat panel detector 405 is cooled by the cooling mechanism through the heat radiator and the thermal connecting unit shown in the foregoing embodiment. Thus, having the flat panel detector 405 fixed to the C-type arm 404 enables capturing more radiation images than is possible with the flat panel detector 405 removed from the C-type arm 404.

FIG. 6B is an example showing a case where radiography is conducted using another radiation generating unit 407 instead of radiation generating unit 401 provided on the C-type arm 404 with the flat panel detector 405 removed from the C-type arm 404, in a mobile radiation imaging apparatus capable of performing fluoroscopic radiography and still image photography. Reference numeral 407 denotes a radiation generating unit mounted in advance. In this application as well, as is the case with the above embodiment, the flat panel detector 405 is capable of deriving images within the maximum number of images of radiation images "n" that is consistent with the heat radiator suppressing a rise in temperature to a temperature at which the flat panel detector is not adversely affected, for example, the flat panel detector 405 can perform a still image photography and a short-time fluoroscopic radiography. In addition, with the flat panel detector 405 fixed to the C-type arm 404, heat generated in the flat panel detector 405 is cooled by the cooling mechanism through the heat radiator and the thermal connecting unit stated in the foregoing embodiment. Thus, having flat panel detector 405 fixed to the C-type arm 404 enables capturing more radiation images than is possible with the flat panel detector 405 removed from the C-type arm 404.

The present invention relates to a radiation imaging apparatus suited for use in medical diagnosis, and in particular, to a radiation imaging apparatus including a flat panel detector composed of a semiconductor element as a detector.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation imaging apparatus comprising:
a flat panel detector for deriving a radiation image based on incident radiation;
a holding unit which holds the flat panel detector; and
a connecting mechanism capable of performing a connecting and a disconnecting between the holding unit and the flat panel detector, wherein the connecting mechanism includes a mechanical connection unit which mechanically connects the flat panel detector to the holding unit and a heat transmitting unit which transmits heat between the flat panel detector and the holding unit, the heat transmitting unit comprising a heat pipe.

2. The radiation imaging apparatus according to claim 1, wherein the connecting mechanism includes further an electric connection unit which electrically connects the flat panel detector to the holding unit.

3. The radiation imaging apparatus according to claim 1, wherein the flat panel detector is provided with a converting unit having a substrate, and having on the substrate a plurality of pixels which act as a converting unit that converts the radiation into an electric signal and transfers the electric signal and a signal processing circuit for processing the electric signal read out from the converting unit.

4. The radiation imaging apparatus according to claim 3, wherein each of the pixels includes a converting element which converts the radiation into an electric signal and a switching element which transfers the electric signal.

5. The radiation imaging apparatus according to claim 4, wherein each of the converting elements includes a scintillator which converts the radiation into light and a photoelectric transducer which converts the light into the electric signal.

6. The radiation imaging apparatus according to claim 1, further comprising a radiation generating apparatus held with the holding unit.

7. A radiation imaging apparatus comprising:
a holding unit which holds a flat panel detector for deriving a radiation image based on incident radiation; and
a connecting mechanism capable of performing a connecting and a disconnecting between the holding unit and the flat panel detector, wherein the connecting mechanism includes a mechanical connection unit which mechanically connects the flat panel detector to the holding unit and a heat transmitting unit which transmits heat between the flat panel detector and the holding unit, the heat transmitting unit comprising a heat pipe.

8. The radiation imaging apparatus according to claim 7, wherein the connecting mechanism includes further an electric connection unit which electrically connects the flat panel detector to the holding unit.

* * * * *